United States Patent [19]

Nishio et al.

[11] Patent Number: 4,923,587
[45] Date of Patent: May 8, 1990

[54] TERMINAL FIXING STRUCTURE FOR A CERAMIC BASE

[75] Inventors: Hisaharu Nishio, Tokai; Hiromichi Hayashi, Nagoya, both of Japan

[73] Assignee: NGK Spark Plug Co., Ltd., Aichi, Japan

[21] Appl. No.: 366,390

[22] Filed: Jun. 15, 1989

[51] Int. Cl.[5] .................... G01N 27/26; H01R 13/428
[52] U.S. Cl. .................................. 204/424; 439/733; 439/913
[58] Field of Search ............ 439/127, 733, 890, 913; 209/429, 427, 428

[56] References Cited

U.S. PATENT DOCUMENTS

| | | | |
|---|---|---|---|
| 4,123,131 | 10/1978 | Pearce et al. | 204/428 X |
| 4,419,212 | 12/1983 | Dietz et al. | 204/427 X |
| 4,556,475 | 12/1985 | Bayha et al. | 204/427 |
| 4,784,743 | 11/1988 | Iino et al. | 204/427 X |

Primary Examiner—Eugene F. Desmond
Attorney, Agent, or Firm—Sughrue, Mion, Zinn, Macpeak & Seas

[57] ABSTRACT

A terminal fixing structure which includes a cylindrical ceramic base with a conductive contact on the side and a metal thermal with a pair of resilient arms for holding the side of the ceramic base and for contacting the conductive contact. The ceramic base has an engaging receptor on the side and each of the arms has an engaging portion for engaging with the receptor. Since the engaging receptor (e.g., ring grooves) of the ceramic base is firmly engaged with the engaging portion (e.g., teeth), the ceramic base and the terminal will not be separated from each other by a vibration, etc. An oxygen sensor using this terminal fixing structure is one possible application.

6 Claims, 7 Drawing Sheets

TERMINAL FIXING STRUCTURE FOR A CERAMIC BASE

BACKGROUND OF THE INVENTION

This invention relates to a terminal fixing structure for a cylindrical ceramic base used in a sensor such as an oxygen sensor.

A general terminal fixing structure for a cylindrical ceramic base with a conductive contact on its surface (e.g., for an oxygen detection element) includes a metal terminal. The terminal has a resilient arm that fits the shape of the ceramic base and engages with the conductive contact on the surface of the ceramic base.

The general terminal fixing structure is used, for example, in an oxygen sensor with a detection element 16 including a pair of porous electrodes 12 and 14 provided on each face of an oxygen ion-conducting solid (e.g., $ZrO_2$) electrolyte 10, in a test-tube shape, as shown in the partially sectional view of FIG. 6 (Japanese Patent Application No. S61-146210 ... ). The oxygen sensor has: a metal member 18; the detection element 16 mounted to the metal member 18 via an insulating ceramic spacer 20, packed talc powders 22, and a ceramic sleeve 24; a protection tube 26 for the detection element 16; a metal terminal 28 connecting to the external electrode 12 of the detection element 16; a metal terminal 32 connecting to the inner electrode 14 of the detection element 16; a metal terminal 33 of an internal ceramic heater 30; leads 34, 36, 38 and 39 respectively connecting to the metal terminals 28, 32, and 33 and to the ceramic heater 30; and housings 40 and 42 for protecting the terminals 28, 32, and so on.

The detection element 16 includes, as shown in FIG. 7, a cylinder 50, a flange 52 engaging with the ceramic spacer 20, and a detection part 54 exposed to the surrounding atmosphere. A conductive contact 56 with the external porous electrode 12, which cannot be seen in FIG. 7 is provided near the opening of the cylinder 50 and is connected to the electrode 12 in the detection part 54 by a lead 58. The electrode 12 in the detection part 54 is covered with a porous protection layer.

The metal terminal 28 for the external electrode includes, as shown in FIG. 7, a pair of curved arms 60 and 62, a holder 64 for holding the lead 34, and a lead 66 for connecting the arms 60 and 62 to the holder 64. The conductive contact 56 of the detection element 16 is held by the resilient arms 60 and 62, thus allowing the metal terminal 28 to be attached to the detection element 16.

The oxygen sensor with this fixing structure is easily manufactured. In this oxygen sensor, an oxygen partial pressure signal generated between the two porous electrodes 12 and 14 of the detection element 16 is outputted from the leads 34 and 36 via the metal terminal 28 for the external electrode and via the metal terminal 32 for the inner electrode, respectively. This oxygen sensor can thus accurately detect the oxygen partial pressure signal without being influenced by noise from an ignition plug or noise caused by a ground voltage, in contrast to another oxygen sensor in which an external porous electrode of a detection element is grounded to an exhaust system via a metal member. An example of the latter oxygen sensor is disclosed in Japanese Patent Publication No. S59-41952.

The terminal fixing structure above, however, has the following problems. Since the terminal 28 is attached to the detection element 16 only by the resilient arms 60 and 62, it might be separated from the element 16 by a vibration of an internal combustion engine, etc, or it might be separated from the element 16 while the oxygen sensor is being assembled if an excessive force applied on the lead 34.

SUMMARY OF THE INVENTION

One objective of the invention is to provide a terminal fixing structure for a ceramic base, in which a connection terminal is firmly attached to the ceramic base.

Another objective of the invention is to provide a terminal fixing structure in which a connection terminal is stably attached to the ceramic base for a long time period.

These and other objectives are realized by a terminal fixing structure including: a cylindrical ceramic base with a conductive contact on the side, and a metal terminal with a pair of resilient arms for holding the side of the ceramic base and for contacting the conductive contact; the ceramic base having at least one engaging receptor on its side, with each of the arms having at least one engaging portion for engaging with the receptor of the ceramic base.

The engaging receptor on the side of the ceramic base may be one or more ring grooves, or projects. An engaging portion is provided at the tip of each arm of the metal terminal for engaging with the above receptor. The engaging portion is, for example, one or more teeth or recesses.

In the present invention, since the engaging receptor (e.g., ring grooves) on the side of the ceramic base firmly engages with the engaging portion (e.g., teeth at the tip of each arm) of the terminal, the ceramic base and the terminal will not be separated from each other by a vibration, and will remain stably connected for a long time period.

DETAILED DESCRIPTION OF PREFERRED EMBODIMENTS

Figure 1:
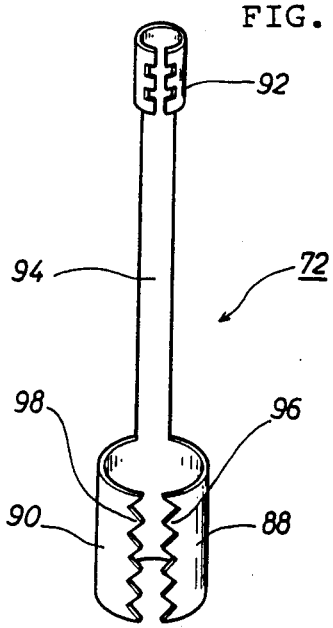
FIG. 1 is a perspective view illustrating a first embodiment of the present invention.
Figure 1:
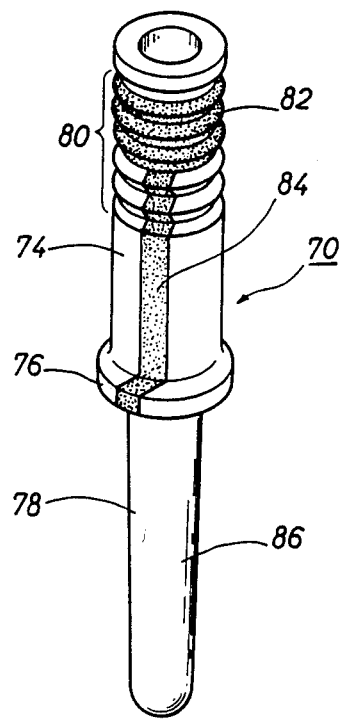
Figure 6:
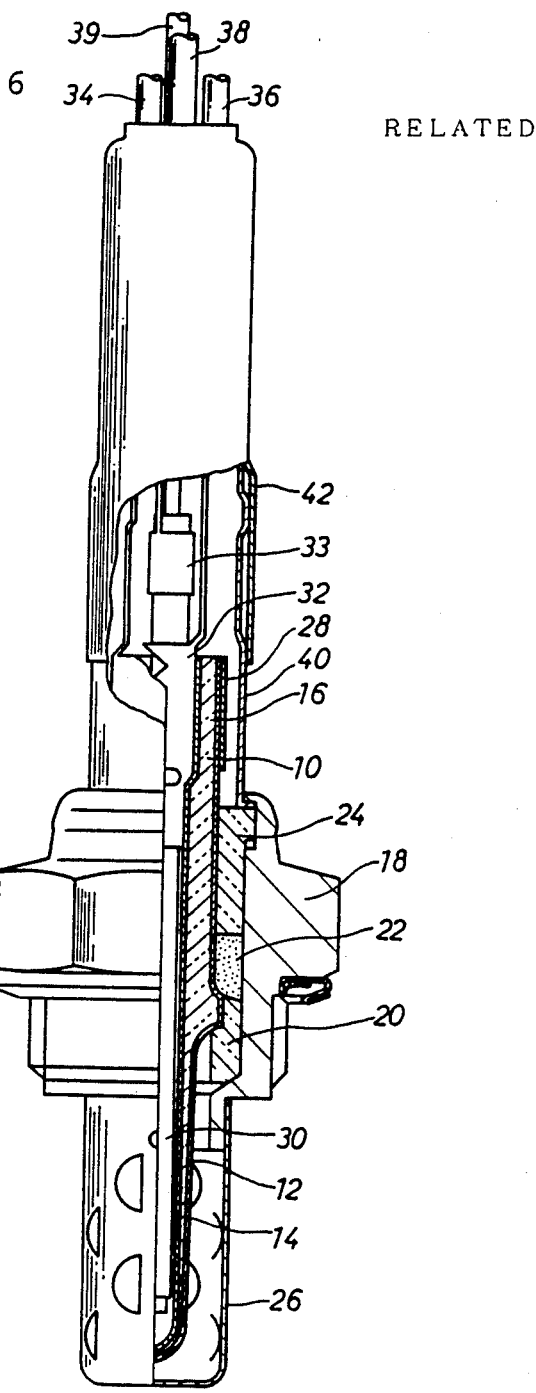
FIG. 6 is a partially sectional view illustrating a general oxygen sensor.
Figure 7:
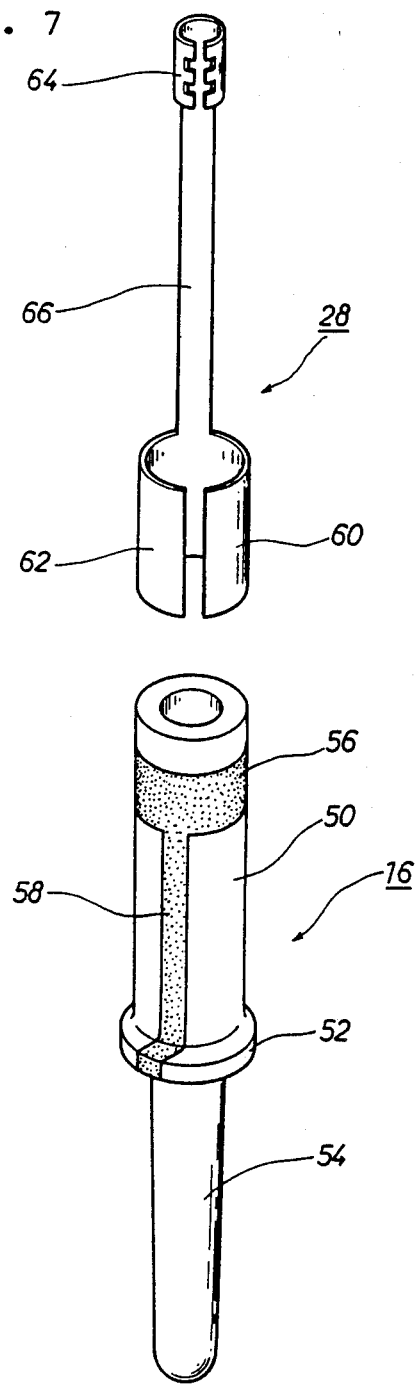
FIG. 7 is a perspective view illustrating a general terminal fixing structure.

In the first embodiment, shown in FIG. 1, the present invention is applied in an oxygen sensor with a test-tube shaped detection element 70. The general constitution of the oxygen sensor of the embodiment is the same as that of the general oxygen sensor shown in FIG. 6, and hence only the constitution of the detection element 70 and that of a metal terminal 72 for an external electrode are described below.

The detection element 70 includes, as shown in FIG. 1, a cylinder 74, a flange 76 engaging a ceramic spacer and a detection part 78 exposed to the surrounding atmosphere. Several ring grooves 80 and a conductive contact 82 covering a part of the grooves 80 are provided near the opening of the cylinder 74. The conductive contact 82 is connected to an external porous electrode of the detection element 70 in the detection part 78 by a lead 84. The external porous electrode in the detection part 78 is covered with a porous protection layer 86 and is not visible.

The metal terminal 72 for the external electrode includes a pair of curved arms 88 and 90, a holder 92 for holding a lead (not shown), and a lead 94 connecting the arms 88 and 90 to the holder 92. Teeth 96 or 98 are provided at the tip of each arm 88 or 90 for engaging with the ring grooves provided on the detection element 70.

The cylinder 74 of the detection element 70 is inserted upward into the space defined by the two arms 88 and 90 of the metal terminal 72, thus allowing the metal terminal 72 to be attached to the detection element 70. Since the resilient arms 88 and 90 firmly engage the teeth 96 and 98 of the metal terminal 72 with the plural ring grooves 80 of the detection element 70, the metal terminal 72 is not be separated from the detection element 70 by a vibration, etc.

Although the embodiment has plural ring grooves 80, one ring groove alone would be sufficient to attain the same effect.

Figure 2:
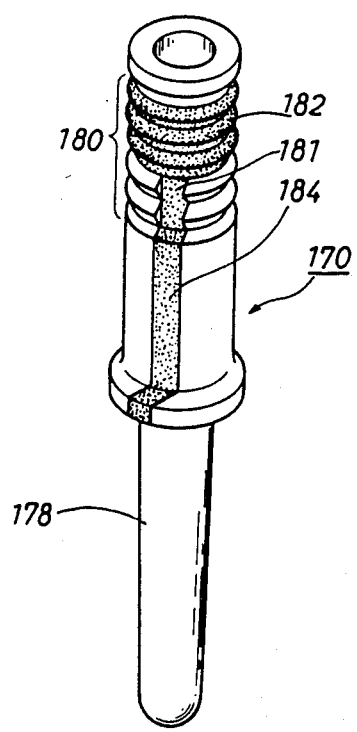
FIG. 2 is a perspective view illustrating a second embodiment of the invention.

In the second embodiment, shown in FIG. 2, the present invention is applied to an oxygen sensor with a test-tube shaped detection element 170. The general constitution of the oxygen sensor of the second embodiment is the same as that of the first embodiment, so only the changes in the detection element 170 will be described hereinafter.

The detection element 170 of the embodiment has a notch 181 in the lower part of ring grooves 180. A conductive contact 182 partially covering the ring grooves 180 connects to an external porous electrode of the detection element 170 in a detection part 178 by a lead 184 running through the notch 181. In addition to the advantages of the first embodiment, the second embodiment has another advantage: the lead 184 will not be scraped off by the teeth of a metal terminal (not shown) when the metal terminal is attached to the detection element 170.

Although the several ring grooves 180 are provided in the embodiment, one ring groove is sufficient to attain the same effect. The notch 181 is only on the lower part of the plural ring grooves 180 in the embodiment, but it could be provided through the full length of the grooves 180 or the full length of a cylinder of the detection element 170.

Figure 3:
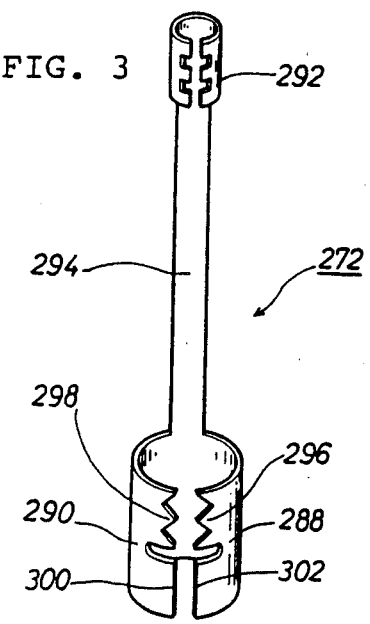
FIG. 3 is a perspective view illustrating a third embodiment of the invention.
Figure 3:
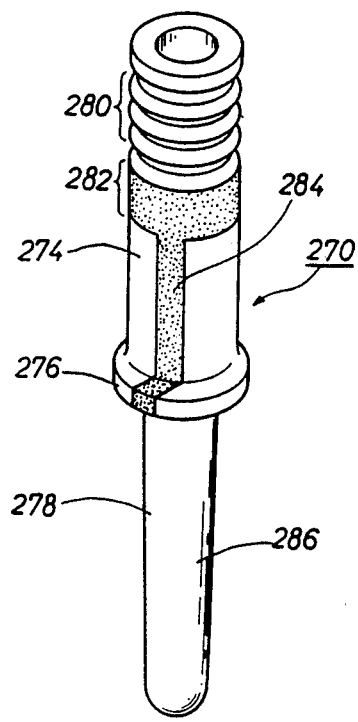

In the third embodiment, shown in FIG. 3, the present invention is applied to an oxygen sensor with a test-tube shaped detection element 270. The general constitution of the oxygen sensor of this embodiment is the same as that of the general oxygen sensor shown in FIG. 6, so only the constitution of the detection element 270 and that of a metal terminal 272 for an external electrode will be described.

The detection element 270 includes a cylinder 274, a flange 276 engaging a ceramic spacer, and a detection part 278 exposed to the surrounding atmosphere. Several ring grooves 280 and a conductive contact 282 encircling a part of the cylinder 274 adjacent to the grooves 280 are provided near the opening of the cylinder 274. The conductive contact 282 is connected to an external ground porous electrode of the detection element 270 in the detection part 278 by a lead 284. The external porous electrode in the detection part 278 is covered with a porous protection layer 286 and is not visible.

The metal terminal 272 for the external electrode includes a pair of curved arms 288 and 290, a holder 292 for holding a lead (not shown), and a lead 294 connecting the arms 288 and 290 to the holder 292. Teeth 296 or 298 are provided on the upper part of the tip of each arm 288 or 290 for engaging with the ring grooves 280 of the detection element 270, and an electrode contact 300 or 302 is provided on the lower part of the tip of each arm.

The cylinder 274 of the detection element 270 is inserted upward into the space defined by the two arms 288 and 290 of the metal terminal 272, thus allowing the metal terminal 272 to be attached to the detection element 270. Since the resilient arms 288 and 290 firmly engage the teeth 296 and 298 of the metal terminal 272 with the ring grooves 280 of the detection element 270, the metal terminal 272 will not be separated from the detection element 270 by a vibration, etc. The electrode contacts 300 and 302 of the terminal 272 do not have teeth, thus preventing the conductive contact 282 or the lead 284 from being accidentally scraped away at the time of attachment.

Figure 4:
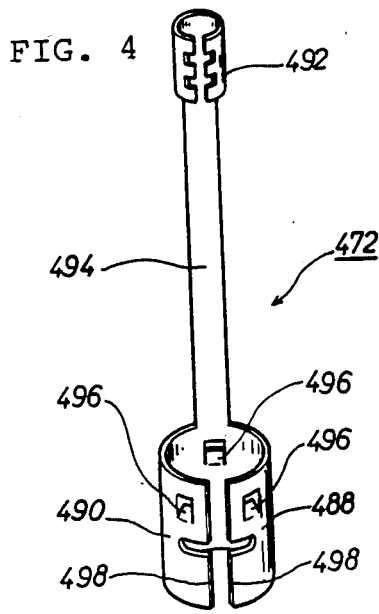
FIG. 4 is a perspective view illustrating a fourth embodiment of the invention.
Figure 4:
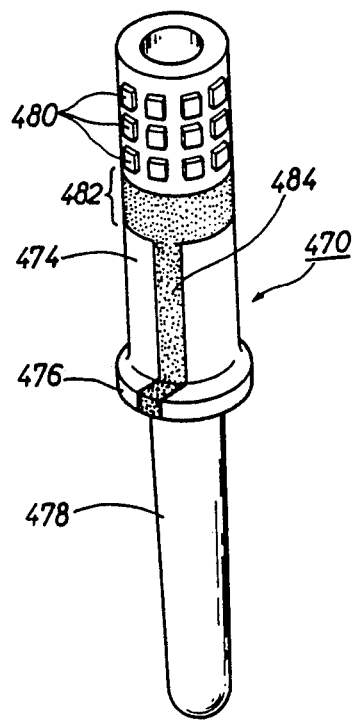

In the fourth embodiment shown in FIG. 4, the present invention is applied to an oxygen sensor with a test-tube shaped detection element 470. The general constitution of the oxygen sensor of this embodiment is the same as that of the general oxygen sensor shown in FIG. 6, so only the constitution of the detection element 470 and that of a metal terminal 472 for an external porous electrode will be described.

The detection element 470 includes a cylinder 474, a flange 476 engaging a ceramic spacer, and a detection part 478 exposed to the surrounding atmosphere. A number of 50-to-10 $\mu$m thick projections 480, formed by a screen print, and a conductive contact 482 encircling a part of the cylinder 474 adjacent to the projects 480 are provided near the opening of the cylinder 474. The conductive contact 482 is connected to an external porous electrode of the detection element 470 in the detection part 478 by a lead 484. The external porous electrode in the detection part 478 is covered with a porous protection layer 486 and is not visible.

The metal terminal 472 for the ground electrode includes a pair of curved arms 488 and 490, a holder 492 for holding a lead (not shown), and a lead 494 for connecting the arms 488 and 490 to the holder 492. Several catches 496 are provided on the upper part of the arms 488 and 490 of the metal terminal 472 for engaging with the projections 480 on the detection element 470, and an electrode contact 498 is provided on the lower part of each arm 488 or 490.

The cylinder 474 of the detection element 470 is inserted upward into the space defined by the arms 488 and 490 of the metal terminal 472, thus allowing the metal terminal 472 to be attached to the detection element 470. Since the resilient arms of the terminal 472 firmly engage the several catches 496 with a number of projections 480 on the detection element 470, the metal terminal 472 will not be separated from the detection element 470 by a vibration, etc.

Figure 5:
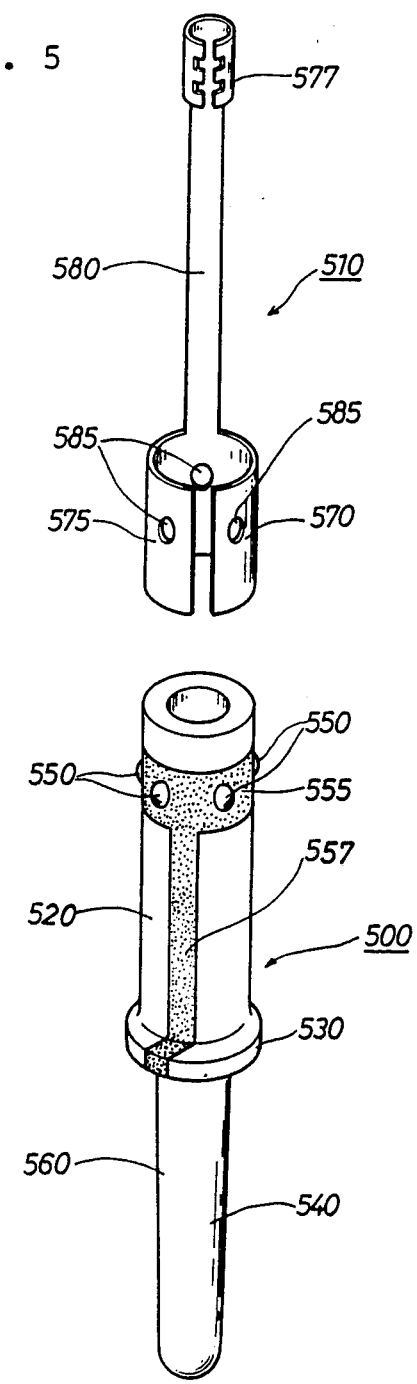
FIG. 5 is a perspective view illustrating a fifth embodiment of the invention.

In the fifth embodiment shown in FIG. 5, the present invention is applied to an oxygen sensor with a test-tube shaped detection element 500. The general constitution of the oxygen sensor of this embodiment is the same as that of the general oxygen sensor shown in FIG. 6, so only the constitution of the detection element 500 and that of a metal terminal 510 for an external electrode will be described. The detection element includes a cylinder 520, a flange 530 engaging a ceramic spacer, and a detection part 540 exposed to the surrounding atmosphere. Several projections 550 and a conductive contact 555 are provided near the opening of the cylinder 520. The conductive contact 555 is connected to an external porous electrode of the detection element 500 in the detection part 540 by a lead 557. The external porous electrode in the detection part 540 is covered with a porous protection layer 560 and is not visible.

The metal terminal 510 for the ground electrode includes a pair of curved arms 570 and 575, a holder 577 for holding a lead (not shown), and a lead 580 for connecting the arms 570 and 575 to the holder 577. Several recesses or holes are provided in the arms 570 and 575 of the terminal 510 to engage with the projections 550 on the detection element 500, and the whole body of each of the arms 570 and 575 works as an electrode contact.

The cylinder 520 of the detection element 500 is inserted upward into the space defined by the two arms 570 and 575 of the metal terminal 510, thus allowing the metal terminal 510 to be attached to the detection element 500. Since the resilient arms 570 and 575 firmly engage the several recesses or holes 585 of the metal terminal 510 with the plural projects 550 on the detection element 500, the terminal 510 will not be separated from the detection element 500 by a vibration, etc.

The present invention may be applied to a glow plug or to other sensors besides the oxygen sensor described in these embodiments. Since there may be many modifications without departing from the scope of the claims, these embodiments are not intended to limit the claims to these embodiments, but are only intended to illustrate the invention more clearly.

What is claimed is:

1. An oxygen sensor comprising:
   a cylindrical ceramic base with a conductive contact on the side,
   a metal terminal with a pair of resilient arms for fastening the side of the ceramic base and for conductively engaging the conductive contact, and
   an oxygen detection element with electrodes comprising an electrode connected to the conductive contact;
   in which the ceramic base has at least one engaging receptor on the side and each of side arms has at least one engaging portion for engaging with the engaging receptor.

2. A terminal fixing structure comprising:
   a cylindrical ceramic base with a conductive contact on the side, and
   a metal terminal with a pair of resilient arms for fastening to the side of the ceramic base and for conductively engaging the conductive contact;
   in which the ceramic base has at least one engaging receptor on the side and each of the arms has at least one engaging portion for engaging with the engaging receptor.

3. A terminal fixing structure according to claim 1, in which the engaging receptor is one or more ring grooves provided along the circumference of the cylindrical base, and the engaging portion is one or more teeth provided at the tip of each arm.

4. A terminal fixing structure according to claim 2, in which the teeth are positioned on each arm so as not to be in contact with the conductive contact.

5. A terminal fixing structure according to claim 1, in which the engaging receptor is at least one projection and the engaging portion is at least one recess or hole.

6. A terminal fixing structure according to claim 1, in which the engaging receptor is at least one projection and the engaging portion is at least one catch.

\* \* \* \* \*